(12) United States Patent
Stecco et al.

(10) Patent No.: US 10,555,766 B2
(45) Date of Patent: Feb. 11, 2020

(54) ACTIVE TENSION BONE AND JOINT STABILIZATION DEVICES

(71) Applicant: PANTHER ORTHOPEDICS, INC., San Jose, CA (US)

(72) Inventors: Kathryn A. Stecco, San Jose, CA (US); Frank P. Becking, Los Gatos, CA (US)

(73) Assignee: PANTHER ORTHOPEDICS, INC., San Jose, CA (US)

( * ) Notice: Subject to any disclaimer, the term of this patent is extended or adjusted under 35 U.S.C. 154(b) by 109 days.

(21) Appl. No.: 15/645,673

(22) Filed: Jul. 10, 2017

(65) Prior Publication Data
US 2017/0311984 A1 Nov. 2, 2017

Related U.S. Application Data

(63) Continuation of application No. PCT/US2016/014125, filed on Jan. 20, 2016.
(Continued)

(51) Int. Cl.
*A61B 17/84* (2006.01)
*A61B 17/04* (2006.01)
(Continued)

(52) U.S. Cl.
CPC ........ *A61B 17/842* (2013.01); *A61B 17/0401* (2013.01); *A61B 17/06166* (2013.01); *A61B 17/683* (2013.01); *A61B 17/844* (2013.01); *A61B 17/80* (2013.01); *A61B 17/8869* (2013.01); *A61B 2017/00526* (2013.01);
(Continued)

(58) Field of Classification Search
CPC ..... A61B 17/68; A61B 17/683; A61B 17/685; A61B 17/686; A61B 17/688; A61B 2017/681; A61B 17/842; A61B 17/844; A61B 2017/0417; A61B 2017/0404; Y10T 24/1498; B65D 63/1027; B65D 63/1036; B65D 63/1063
See application file for complete search history.

(56) References Cited

U.S. PATENT DOCUMENTS

| 3,186,047 A | * | 6/1965 | Schwester | .......... B65D 63/1036 24/16 PB |
| 4,377,872 A | * | 3/1983 | Daniell, Jr. | ............. A41F 9/002 2/321 |

(Continued)

FOREIGN PATENT DOCUMENTS

| CN | 1631325 A | 6/2005 |
| DE | 19527151 | 1/1997 |

(Continued)

OTHER PUBLICATIONS

WO, PCT/US2016/014125 ISR and Written Opinion, dated May 13, 2016.
(Continued)

*Primary Examiner* — Amy R Sipp
(74) *Attorney, Agent, or Firm* — One LLP

(57) ABSTRACT

Systems and methods of manufacture for bone and joint stabilization devices are described for such devices that are tensioned after anchoring during a medical procedure and remain active in maintaining axial tension for continued compression of the subject anatomy.

11 Claims, 8 Drawing Sheets

Related U.S. Application Data

(60) Provisional application No. 62/171,118, filed on Jun. 4, 2015, provisional application No. 62/107,731, filed on Jan. 26, 2015.

(51) Int. Cl.
*A61B 17/06* (2006.01)
*A61B 17/68* (2006.01)
*A61B 17/80* (2006.01)
*A61B 17/88* (2006.01)
*A61B 17/56* (2006.01)
*A61B 17/00* (2006.01)

(52) U.S. Cl.
CPC .............. *A61B 2017/0404* (2013.01); *A61B 2017/0417* (2013.01); *A61B 2017/0461* (2013.01); *A61B 2017/0618* (2013.01); *A61B 2017/564* (2013.01); *A61B 2017/681* (2013.01)

(56) References Cited

U.S. PATENT DOCUMENTS

| | | | |
|---|---|---|---|
| 4,688,561 A * | 8/1987 | Reese | ............ A61B 17/683 606/329 |
| 4,959,064 A | 9/1990 | Engelhardt | |
| 5,258,015 A | 11/1993 | Li et al. | |
| 5,415,660 A | 5/1995 | Campbell et al. | |
| 5,500,018 A | 3/1996 | Spotorno et al. | |
| 5,549,619 A | 8/1996 | Peters et al. | |
| 5,810,854 A | 9/1998 | Beach | |
| 6,093,190 A | 7/2000 | Mattchen | |
| 6,293,949 B1 | 9/2001 | Justis et al. | |
| 6,656,184 B1 | 12/2003 | White et al. | |
| 7,008,429 B2 | 3/2006 | Golobek | |
| 7,235,091 B2 | 6/2007 | Thornes | |
| 7,285,086 B2 | 10/2007 | Smith et al. | |
| 7,833,256 B2 | 11/2010 | Biedermann et al. | |
| 7,875,057 B2 | 1/2011 | Cook et al. | |
| 7,985,222 B2 | 7/2011 | Gall et al. | |
| 8,048,134 B2 | 11/2011 | Partin | |
| 8,348,960 B2 | 1/2013 | Michel et al. | |
| 8,449,574 B2 | 5/2013 | Biedermann et al. | |
| 8,491,583 B2 | 7/2013 | Gall et al. | |
| 8,597,300 B2 | 12/2013 | Deffenbaugh et al. | |
| 8,771,316 B2 | 7/2014 | Denham et al. | |
| 8,828,067 B2 | 9/2014 | Tipirneni et al. | |
| 2002/0091391 A1 * | 7/2002 | Cole | .............. A61B 17/0401 606/916 |
| 2005/0085815 A1 | 4/2005 | Harms et al. | |
| 2005/0203519 A1 | 9/2005 | Harms et al. | |
| 2006/0195103 A1 | 8/2006 | Padget et al. | |
| 2006/0264954 A1 | 11/2006 | Sweeney, II et al. | |
| 2008/0275555 A1 | 11/2008 | Makower et al. | |
| 2010/0094347 A1 | 4/2010 | Nelson et al. | |
| 2010/0211071 A1 | 8/2010 | Lettmann et al. | |
| 2010/0292793 A1 | 11/2010 | Höglund | |
| 2011/0125194 A1 | 5/2011 | Anwand et al. | |
| 2012/0203284 A1 | 8/2012 | Khanna | |
| 2012/0232597 A1 | 9/2012 | Saidha et al. | |
| 2013/0079776 A1 | 3/2013 | Zwirkoski et al. | |
| 2013/0261625 A1 | 10/2013 | Koch et al. | |
| 2014/0100573 A1 | 4/2014 | Llas Vargas et al. | |
| 2014/0228883 A1 | 8/2014 | Blain | |
| 2014/0257294 A1 | 9/2014 | Gédet et al. | |
| 2015/0045794 A1 | 2/2015 | Garcia et al. | |
| 2015/0238232 A1 | 8/2015 | Biedermann et al. | |
| 2016/0200947 A1 | 4/2016 | Carvani et al. | |

FOREIGN PATENT DOCUMENTS

| | | |
|---|---|---|
| JP | 2003-220071 A1 | 8/2003 |
| WO | WO 2008/016910 A2 | 2/2008 |
| WO | WO 2014/149244 A1 | 9/2014 |

OTHER PUBLICATIONS

EP, 16743868.8 Extended Search Report, dated Dec. 8, 2017.
CN, 201680007323.0 Office Action, dated Sep. 29, 2019.
JP, 2017-557276 Office Action, dated Oct. 21, 2019.

* cited by examiner

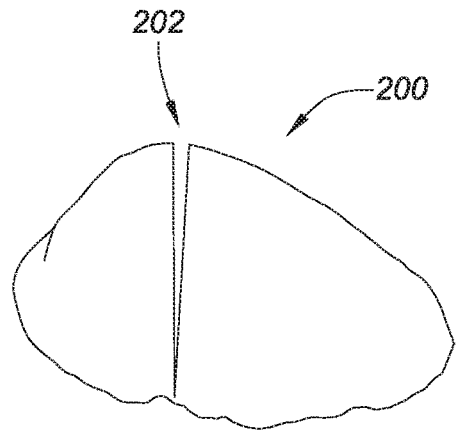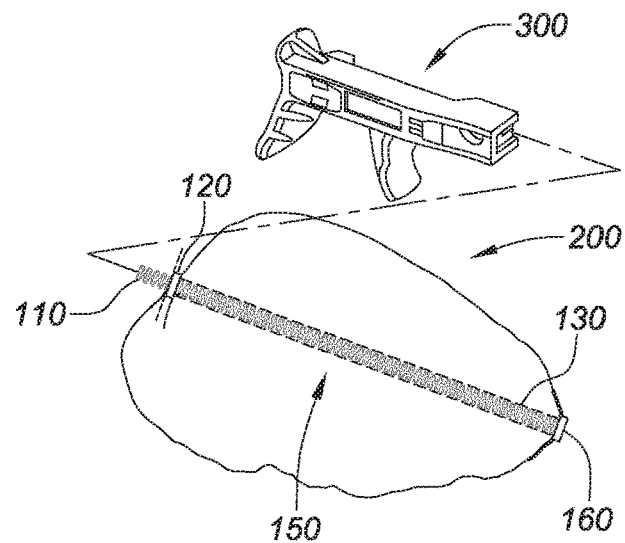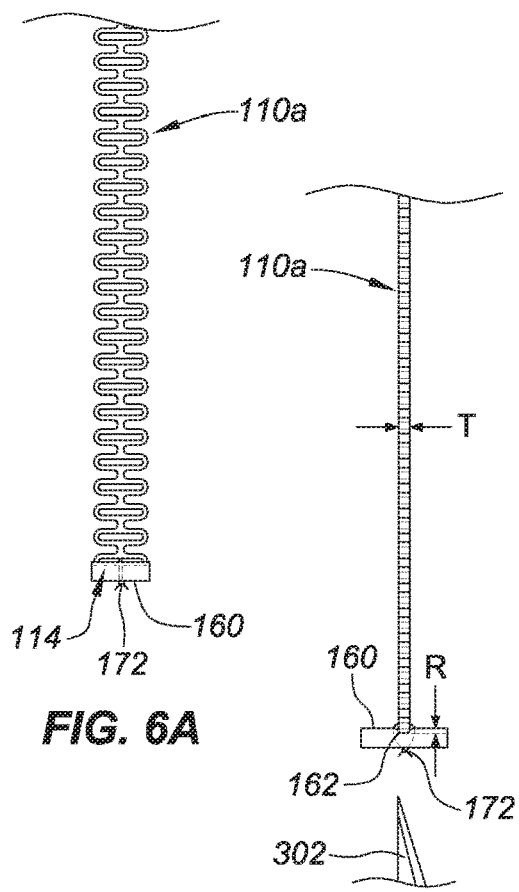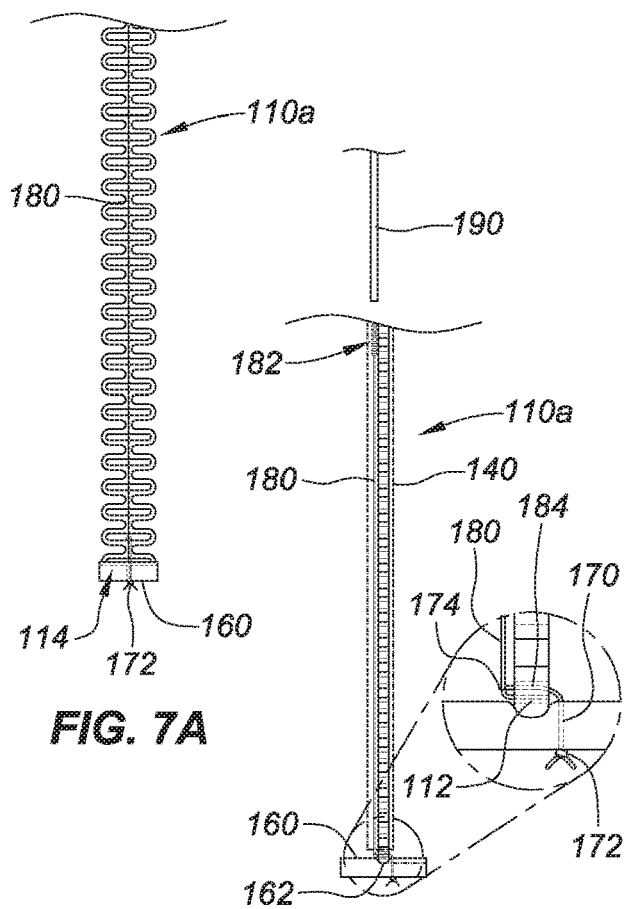
FIG. 5A   FIG. 5B
FIG. 6A   FIG. 6B   FIG. 7A   FIG. 7B

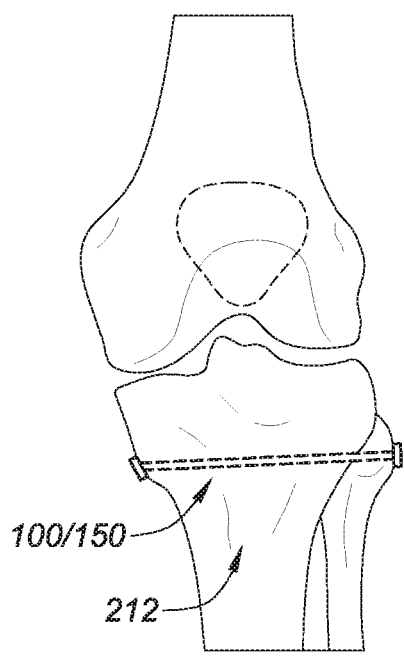
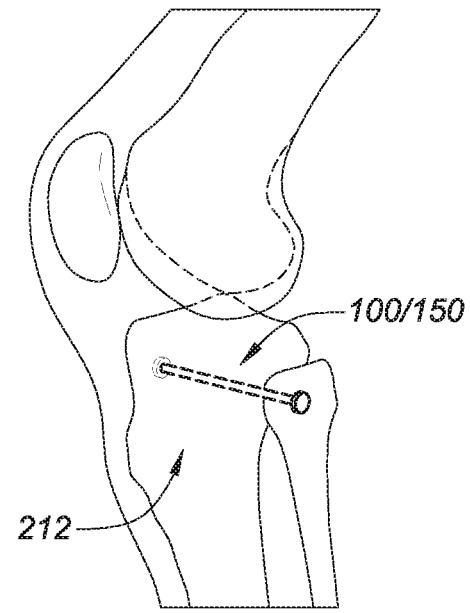
FIG. 11A  FIG. 11B
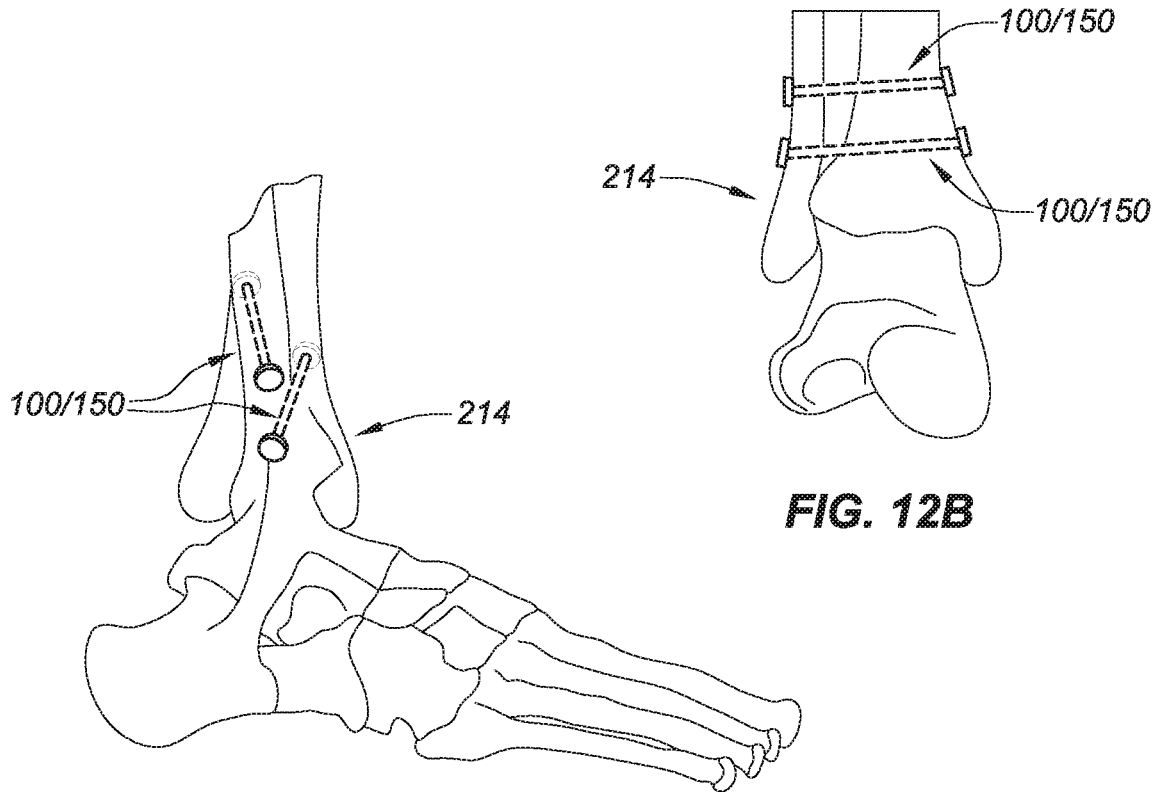
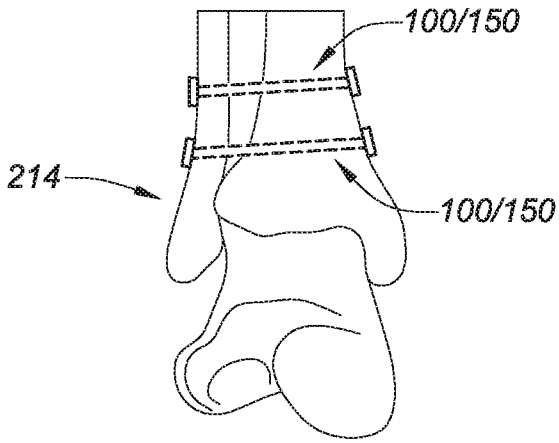
FIG. 12A  FIG. 12B

ACTIVE TENSION BONE AND JOINT STABILIZATION DEVICES

CROSS-REFERENCE TO RELATED APPLICATIONS

This filing is a continuation of PCT Application No. PCT/US16/14125, filed Jan. 20, 2016, which claims priority to and/or the benefit of U.S. Provisional Patent Application Nos. 62/107,731, filed Jan. 26, 2015, and 62/171,118, filed Jun. 4, 2015, all of which are incorporated by reference herein in their entireties for all purposes.

FIELD

The embodiments described herein are related in the field of surgery and, more particularly, methods for bone fusion, joint stabilization, and/or fracture fixation surgery.

BACKGROUND

Various devices have been employed in orthopedic surgery for bone fusion and/or joint stabilization. Bone screws, staples and plates have served as a set of rigid options. Per U.S. Pat. Nos. 4,959,064; 6,656,184; 7,833,256; 7,985,222; 8,048,134; 8,449,574 and 8,491,583 and USPPN 2006/0264954 some screw-type devices have incorporated tensioning springs or members. Button-and-suture type devices have provided a more flexible set of options. U.S. Pat. Nos. 7,235,091, 7,875,057 and 8,348,960 offer examples of such device and suitable applications therefor.

Various pros-and-cons are associated with the above options. The subject embodiments seek to address many shortcomings of existing products as elaborated upon below and as may be further appreciated by those with skill in the art.

SUMMARY

Bone and joint stabilization devices are described that are tensioned during a medical procedure and remain active in maintaining axial tension for continued compression of the subject anatomy during use. In the subject embodiments, an orthopedic surgery system comprises an elongate spring member comprising a plurality of beams, each including a lateral component free to deflect for stretching the spring member axially, and at least one anchoring head adapted to receive the spring member and secure it with a ratcheting interface. Two such heads may be used with one on each side of the elongate spring member. Alternatively, one head may be used along with a foot to anchor an opposite end of the spring member. The anchoring head(s) may retain a low profile while incorporating two teeth for spring member engagement by virtue of an opposite facing tooth support configuration.

If a distal foot is provided in the system or as part of a sub-assembly, the foot may be adapted to rotate from a position aligned with the spring member to a position transverse to the spring member. In which case, the device can be implanted through a minimum-diameter hole or channel spanning the bone, joint space, or fracture, in the former configuration and then secured or stabilized in the latter configuration.

In many cases, it will be desirable to remove the device after sufficient healing has occurred and the implant is no longer necessary. When the foot is secured to the spring member by filament(s) or cord (one or the other alternatively referred to as a "strand"), the strand member or members may be cut to facilitate removal of the device. Alternatively, the filament(s) or cord may loop-through the spring member and be held by a rod until the rod is pulled to effect release. Either mechanism can facilitate removal of the device, via minimal incision, once its goal has been accomplished. Total removal may be an important endpoint for some patients and providers as retained implants can create adverse reactions.

The rod may include a proximal threaded interface for connection to an extraction tool. The distal end of the rod may be bent or curved with an extension set to interface with the spring member to avoid twisting and/or inadvertent release. In which case, the rod advantageously comprise Nitinol that is superelastic (SE) at body temperature (i.e., having an $A_f$ below about 37° C.) so that its distal end may be pulled from such location or engagement without fracture.

The anchoring foot may comprise a body with an oval or rectangular planform shape. Generally, its height and overall size will be minimized, while still maintaining adequate surface area for load bearing. It may include a transverse groove to act as a pivot with the spring member. It may be relieved over or along one face to accommodate or nest with the elongate member for a reduced crossing profile for insertion or implantation. The anchor foot may be biased towards a transverse position (e.g., by an integral or a supplemental spring) to transition easily from its axial delivery configuration to its implanted position against the cortex on the far side. Alternatively, one or more filaments or pull wires may be employed to accomplish foot rotation. Foot shape may further (or alternatively) assist in this regard.

Whether a pair of head-type anchors are used, or one head anchor and one foot anchor is used, various features may be included in the system to assist with device removal after implantation. Namely, a sheath may be provided over the spring member to avoid bone or other tissue ingrowth. The sheath may comprise a biocompatible polymer such as PTFE. A higher strength polymer such as PEEK or metal hypotube (e.g., Nitinol or Stainless Steel) may be selected if additional shear strength is desired for the sheath. Especially with the polymer examples, the sheath may be trimmed to length during a medical procedure. Alternatively, a physician may select a pre-cut sheath from a group or panel of such items. In another approach, the elongate member itself may be polymer coated. Such coating may be accomplished by electrostatic (i.e., powder coating), spray or dip coating or as otherwise. The coating may form webbing portions between adjacent beams in the spring.

As for the elongate spring member itself, it preferably includes features for flex, anchor means securing (e.g., setting anchors in place at a final or near-final treatment position) and ultimate tightening (e.g., by ratcheting adjustment) to desired or selected tensile force by a physician. Such features are integrated in the embodiment(s) shown. In these, lateral beams or bars arranged in opposing pairs are connected to each other at an outer extent. Each such pair may be connected to the next adjacent pair by a medial connector or bridge.

The beam pairs may each define an aperture or through-hole that can receive and secure or lock the tooth or pawl of a zip head anchor in a gap. In which case, the tooth or teeth in a given anchor head will interface directly with the beams.

The elongate spring member and its beams advantageously comprise NiTi alloy that is superelastic (SE) in use at human body temperature (e.g., has an $A_f$ of about 37° C. or less). Accordingly, the spring member may be designed and the material heat treated so that it exhibits superelasticty when stretched and in use. Otherwise, the NiTi alloy may be selected or processes so that its potential shape-memory (SMA) effect is used in an embodiment, such that the alloy is heat-activated to turn at least partially phase-transform and tighten (or tighten further) once emplaced. Alternatively, the spring member may comprise a high performance or so-called "engineering" polymer such as PEEK. Other materials (especially those with high reversible stain potential such as Beta titanium alloy) might be employed as well.

The spring member is advantageously substantially flat. As such, it may have an aspect ratio of width to thickness of between about 10 to 1 and about 30 to 1. Such a form factor minimizes manufacturing complexity and cost in that the spring member may then be cut (e.g., laser cut, water jet cut or etched) from flat wire, strip or plate. The cut part can be media blasted, pickeled and/or electropolished for surface finish.

Methods of system use and manufacture are contemplated herein. In a method of manufacture for an orthopedic surgery system, stock material is cut into a linear spring pattern. Per above, such cutting may be by laser, water jet cutting or etching. Forming an anchor head (e.g., by injection molding, micromachining, 3D printing or otherwise) adapted to fit and interact with the spring member is likewise contemplated. These parts may be provided in packaged combination in a kit to be acquired. Then in an assembly step (i.e., usually carried out by a physician in situ), the spring member is received within at least one anchor head with a tooth or teeth thereof engaged with through-hoes in the spring member. Advantageously, the through holes are in the spring pattern. This allows for the longest active length of the spring and the prospect of longer axial or linear expansion at lower strains.

In a method of use, an elongate spring member is advanced through a hole drilled through bone or other tissues and set with a distal end distal to a first bone portion and a proximal end proximal to a second bone portion. Then, both ends are secured, with at least one of the ends secured with an anchor including a ratcheting interface. In one embodiment a foot is used at a distal end to secure that end, and a zip-type anchor head used at the proximal end to secure the other end. In another embodiment, two zip heads are used. The spring member is then pulled through the ratcheting interface (of an anchor head at one or both sides) tensioning the spring member, typically, with the anchoring members or means set in place. The spring member may then be trimmed, cutting off any protruding material. The tensioning and/or trimming may be performed using an adapted zip-tie gun or it may be done manually with hand tools. In any case, no rotary or twisting motion of threads is employed in tensioning or setting anchor final position. Without the requirement for any twisting or turning of threads to tension (as opposed to existing spring-type screw devices) linear pull on the spring member is instead employed. Accordingly, once tension is set, in some cases the system can be rotated to a preferred position to take advantage of flexibility considerations (e.g., as referenced below) without altering or substantially altering device tension.

In one example, each end of the spring member is secured with opposite-facing ratcheting anchor members. In another example, the distal end is secured with a foot that is initially positioned aligned with the spring member during advancement through a drill hole, which then turns or pivots to secure the distal end. The foot may be spring-loaded for such effect.

As another option, the spring member may be covered by a sheath to prevent tissue ingrowth as mentioned above. The sheath may be advanced over the spring member once it is in place (before proximal anchor placement). Alternatively, it may be used to support the spring member for advancement into place. The sheath may be trimmed to desired length before or after any such activity, or it may be selected from a panel of different length pre-trimmed sheaths.

The sheath may be removed as part of an overall orthopedic injury treatment method with the spring member after healing. Or it may be left in place, serving the purpose of allowing removal of the spring member as part of this or these method(s), or as a separate removal procedure method.

Likewise, if a foot is included in the system it may be separated from the spring member as part of an overall treatment or subsequent removal method. This may be accomplished by cutting filament(s) or a cord member or members holding or tying the foot onto the spring element. A scalpel accessing from the distal side of the device may be used for this purpose. The foot could then be removed through a separate small incision.

Alternatively, the filament(s) or cord may be released by pulling a rod in the case where the member(s) are looped through the spring element for securing the foot. The rod may include a threaded proximal interface for attaching a threaded cannula thereto from the proximal side of the device and pulling the rod, thus facilitating device removal through the original incision without requirement for new incision on the distal side. This represents another advantage over current flexible devices (i.e., button-and-suture systems) and allows safe application in additional anatomical regions.

The subject devices, kits in which they are included (with or without assembly), methods of use (e.g., implantation, during treatment of a patient while mending and/or for system removal) and manufacture (including assembly of the constituent components in vivo or ex vivo) are all included within the scope of the present disclosure. Some aspects of the same are described above, more detailed discussion is presented in connection with the figures below.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 3B-3E are side-sectional views of anchor heads as may be incorporated in the system in FIG. 2 or otherwise.

FIG. 5A is a side view of a model of a fractured navicular bone; FIG. 5B illustrates the model in FIG. 5A treated using an embodiment of the subject system.

FIGS. 6A and 6B are partial front and side views, respectively, of a distal anchor embodiment hereof; FIGS. 7A and 7B are partial front and side views, respectively, of a mechanically releasable distal anchor embodiment hereof.

FIGS. 8-14 are anatomical illustrations including various views showing methods of embodiment system use in orthopedic injury treatment procedures including: fixation of a fifth metatarsal fracture (FIG. 8), treating a Lisfranc midfoot ligamentous injury (FIG. 9), fixation of a calcaneal osteotomy for a foot reconstructive procedure (FIG. 10), fixation of a proximal tibio-fibular joint injury (FIGS. 11A and 11B), fixation of a distal tibiofibular syndesmotic injury (FIGS. 12A and 12B), fixation of various severity acromioclavicular joint injuries (FIG. 13), and fixation of a clavicle fracture (FIG. 14).

DETAILED DESCRIPTION

Various exemplary embodiments are shown in the figures and further described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present invention. All such modifications are intended to be within the scope of the claims made herein.

Figure 1A:
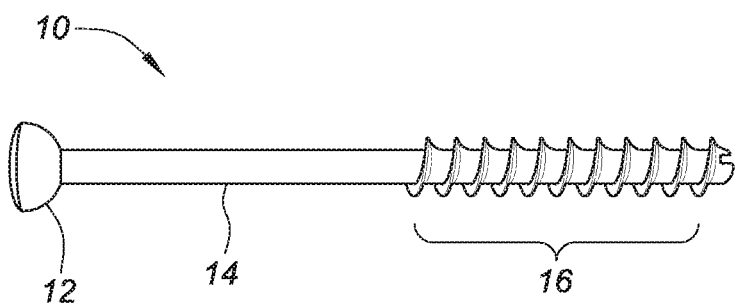
FIGS. 1A and 1B are side-perspective views of existing orthopedic fixation devices.
Figure 1B:
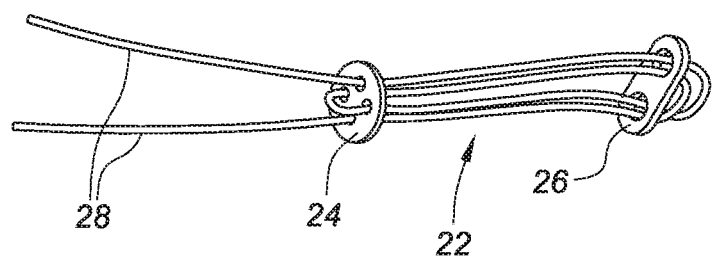

Regarding FIGS. 1A and 1B, these illustrate existing orthopedic fixation systems. A typical bone screw 10 is shown in FIG. 1A. The bone screw includes a head 12, shaft 14 and threaded section 14. While the device has sufficient strength and stiffness to hold bone fragments together after fracture or osteotomy fixation, compression of the fragments (generally necessary for healing) is typically limited and temporary. Furthermore, a stiff metallic device, like a screw, in a bone can also create severe adverse reactions including but not limited to screw migration in and/or out of the bone, osteoarthritis, muscle atrophy, nerve damage, pain, bleeding, bone loss, osteonecrosis and/or secondary fractures due to stress concentration and bone stress at the margins of the stiff screw.

A suture-button type device 20 is shown in FIG. 1B. It includes suture 22, a proximal button 24 and a distal button 26. In use, the proximal free ends 28 of the suture are tied-off (manually or a self-locking feature may be employed) to secure the device after tightening. Such a device allows reduction of a joint, limiting widening of the joint along with allowing some rotational motion after fixation. It also allows application of some manual (difficult to measure or replicate) compression. However, the device is limited by creep and wear of the suture which is known to stretch in a biologic environment. Also, there is no continuous compression beyond what is set at the time of application. Thus, the device can loosen with time, limiting its application to the few joints that have very little motion.

Ultimately, neither of these devices provides continual or continuous compression to the treatment site. Rather, their tension is set and any migration or loosening of features results in loss of tension and/or slack.

Figure 2:
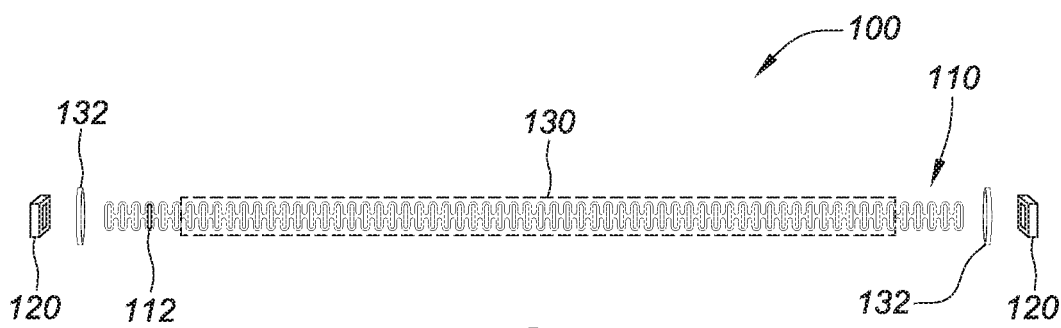
FIG. 2 is a front view of an embodiment of the subject device and/or system.

In contrast, system 100 shown in FIG. 2 is designed for installation, followed by tensioning where that tensioning persists as stored energy in a/the spring member 110. In addition, system 100 can be implemented in a smaller profile where only its elongate spring member 110 need pass through a drill hole (as opposed to a distal button end 16 and/or threaded section 16 that cuts deeply into bone).

Spring member 110 is advantageously designed with the hybrid function of interfacing with securing the system anchors holding the device and providing overall tension. As shown in FIG. 2, two identical anchor heads 120 may be used on each side of the spring member. The spring member may be received within an optional sheath 130 as elaborate upon below. Optional washers 132 may be interposed as tissue interface elements. The washers may be flat or be configured as a "star" type or another type of lock washers to help prevent rotation among/between members. Similarly, spikes, splines or studs may be integrated (by molding, screw-in or otherwise) into the anchor head(s)—typically at underneath and/or around is lower perimeter.

The zip anchors or anchor heads may be variously configured. They may be generally square or rectangular in plan form or shape as shown in FIG. 2. Alternatively, they may be configured as round or circular bodies. Elliptical and/or other shapes may be employed as well.

Figure 3A:
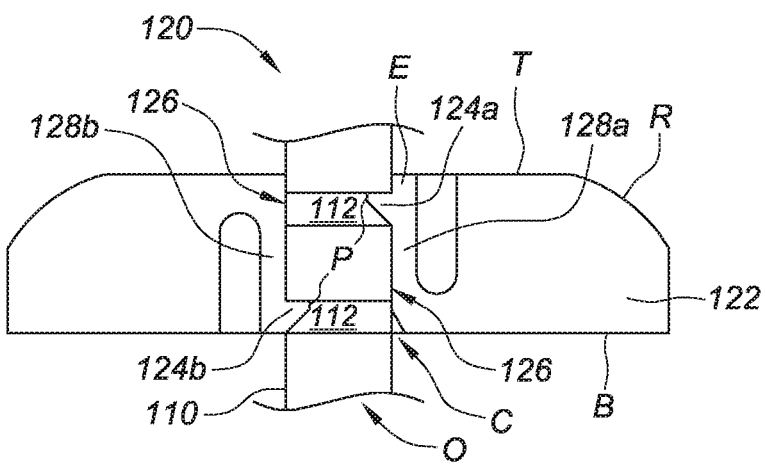
FIG. 3A is a side-sectional view of a "zip" type anchor head including two teeth with a spring member received therein.
Figure 3B:
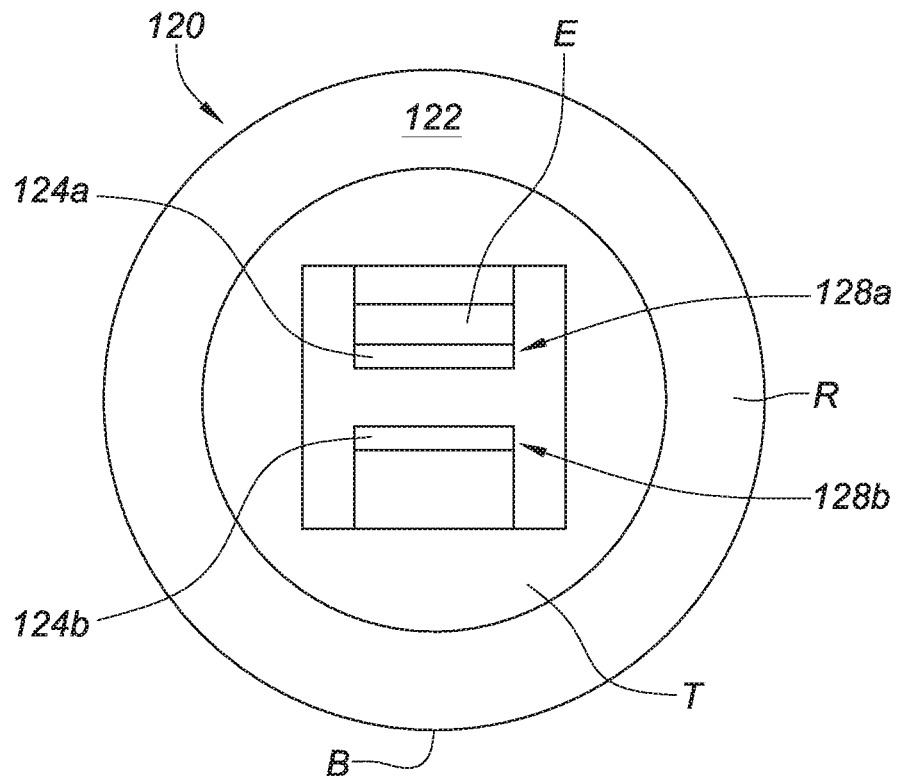
FIG. 3B is a top view of an optional configuration of the anchor head in FIG. 3A without the spring member in place.

The cross section of anchor head 120 shown in FIG. 3A may be representative of any such case. However, FIG. 3B provides a top-view detail of such an anchor or anchor head embodied in a round or circular form.

In each view, anchor device 120 includes a body 122 with two teeth 124a and 124b. The teeth are not stacked vertically as common in other zip tie heads. Rather, the teeth are position on opposite sides of the anchor body and, thus, on opposite sides of the spring member 110 when it is in place as an assembly. Moreover, the teeth are not directly across from one another. Each tooth 124a, 124b is staggered and positioned so an engaged spring member 110 is faced by a support section 126.

As such, an engaged spring member lies or abuts against solid material. Tension on the spring member when engaged with the anchor (i.e., pulling on each tooth) is thereby isolated from lateral load/effect of the other tooth so the elongate members or beams 128a, 128b support each tooth (optionally) via (essentially) pure tensile or compressive load. This simplification of loading may provide additional component strength and helps enable low-profile component design.

To achieve this goal, the elongate members and tooth surface angles for locking with a/the spring member(s) are setup at orthogonal angels. Otherwise, the members (i.e., beam/tooth combinations) may be slanted or angled to draw or pull inwardly in stable equilibrium under spring member 110 tension with backing of the spring member by support section 126. This result can be achieved (at least to some degree) with the configuration shown in FIG. 3A by application of typical draft angles for molding to the part.

Regardless, the elongate support members 128a and 128b are setup or configured as cantilever or cantilevered beam elements with respect to body 122. A general up/down or opposing orientation or plan for tooth and elongate member connection to the body 122 is contemplated. Stated otherwise, one beam carrying a tooth or tooth section is connected to the body of the zip anchor at or adjacent its bottom (B) and another is connected at or adjacent to its top (T)—wherein such designation is made for the anchors 120 in relation to the spring member 110 with which it interfits. Described in yet another manner, the elongate support members are each directed inwardly with respect to the outer surfaces of the anchor.

To elaborate, the so-called "bottom" surface is that which the spring member is first fed through (note feed opening (O) and relief chamfer or cutaway (C) provided for such purpose) in use. The "top" surface is across which the spring member is cut or trimmed after tensioning. Similarly, one tooth (124a) may be regarded as an/the upper or top tooth, and the other tooth (124b) regarded as a/the lower or bottom tooth.

An optional radiused or curved rim (R) around the top of the body advantageously provides as an atraumatic interface to the anchor for reduced trauma to surrounding tissues. Such a radius may be applied to circular body as shown in FIG. 3B and/or other planform shapes as in the square-body anchor in FIG. 2 or others. The radius will typically not intersect and/or reduce material of the elongate tooth-support members so to avoid loss of their strength. In the example shown in FIGS. 3A and 3B (taken together, optionally regarded as having a pan or button-head shaped body), the anchor is approximately 0.25 inches in diameter, 0.060 inches tall (i.e., as measured between the faces) with a rim radius of 0.006 inches.

Another advantageous (but optional) feature concerns the placement of the upper tooth within body 122. As shown, the tooth 124a is configured and/or otherwise positioned so that when spring member 110 is engaged with its support surface on the tooth that one full beam width (W), as discussed below, is set within the zip anchor body. This relationship of elements facilitates trimming spring member 110 at a bridge 132 cleanly or evenly across the zip anchor top (e.g., with flush cutters as a separate tool or as integrated in a multi-function tensioning and trimming tool). Moreover, elongate beam member 128a may include an extension (E) passing beyond its tooth 124a that bottoms-out against an opposing beam 116 (also discussed below) when engaged with the spring member 110. Such a relationship may be useful for maintaining stable tooth position when the spring member is tensioned.

Yet another option is to terminate the teeth at a sharp or an angled edge (not shown) or include a flat terminal face or passing surface (P) thereto. The latter configuration can protect against scoring or scraping (i.e., liberating particulates) from the teeth when passing the spring member through the anchor body.

In any case, the teeth 124a, 124b and apertures or cutouts 112 in the spring member are adapted to work together in a ratchet-type interface. Notably, to interfit with the cutouts 112 in the spring member 110 and include two vertically stacked teeth, such a zip anchor (i.e., one with same-side vertically stacked teeth) would have to be twice as tall as a single tooth design (i.e., be 2 T vs. 1 T in height). In contrast, an up/down tooth and support beam design shown in FIGS. 3A and/or 3B may be regarded as one-and-a-half times the height (i.e., 1.5 T).

Anchor head 120 is advantageously formed by injection molding in plastic. Biocompatible polyamide (Nylon) or polyethelketone (PEEK) may be used for such purposes. Other injection moldable anchor variations are shown in cross section in FIGS. 3C and 3D.

Figure 3C:
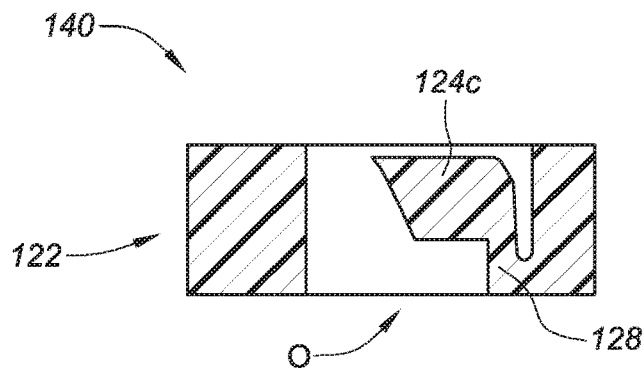

In FIG. 3C, an injection molded anchor head 140 is formed with a plastic body 122 having a single tooth 124c. Tooth 124c pulls inward (i.e., down and to the left as shown in the drawing) given its overhanging configuration at/from its support 128 when engaged with a spring member under tension. Such an approach provides a lock in stable equilibrium. Other than presenting a single-tooth variation, the relative dimensions of elements included in head 140 may match or track with those of commercially-available zip tie head(s).

Figure 3D:
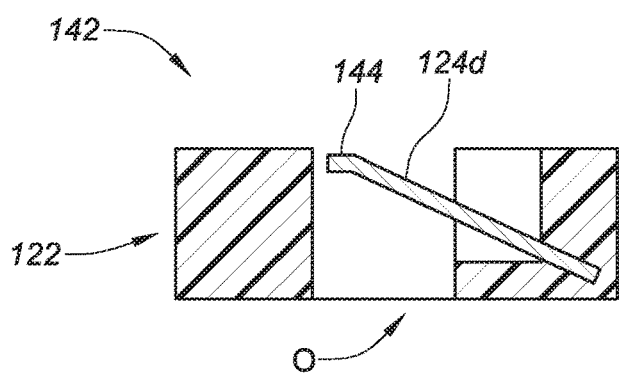

The anchor head 142 in FIG. 3D includes a polymer body 122 and a metal tang or tooth 124d that functions similarly to that in anchor head 140 (in that tooth 124d pulls down-and-in when under spring member tension). However, this embodiment is dimensioned quite differently than an off-the-shelf metal tooth zip tie head. For one, an end 144 of tooth 124d is advantageously positioned so that it will abut an opposing wall support section 126 of the anchor body 122 when engaged with a spring member (not show). Such an arrangement provides significantly more strength to the engagement interface. Furthermore, end 144 may be angled or flattened (as shown) to provide an interface that "bites" better into support section 126 upon spring member tensioning. Still further, although the tooth may be made of stainless steel (as in existing metal-tooth zip tie heads), tooth 124d is more preferably made from SE Nitinol. SE Nitinol will allow greater flex in a thicker tooth body without plastic deformation. Use of a thicker tooth body may provide greater strength and/or the opportunity to include an extension feature (E) like that shown in the FIG. 3A/3B embodiment. In any case, tooth 124d is advantageously co-molded with body 122 in plastic as in typical of metal-tooth zip ties.

Figure 3E:
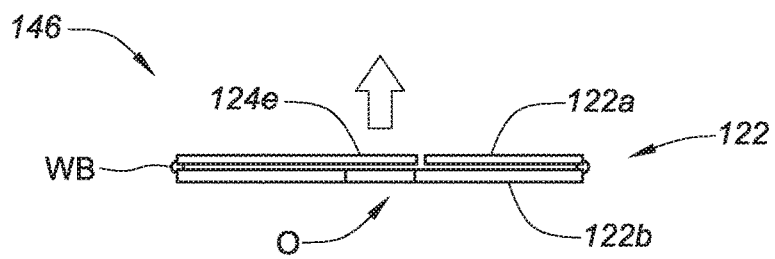
Figure 3F:
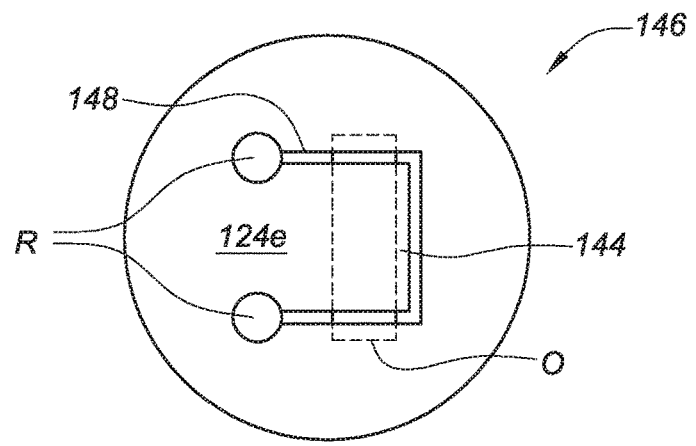
FIG. 3F is a top view of an optional configuration of the anchor head in FIG. 3E.

FIGS. 3E and 3F illustrate a significantly different type of anchor head 146. It is advantageously produced in SE Nitinol, with a tooth 124e formed in a top piece 122a mated to a base piece or frame 122b. These may be attached to one another with a perimeter laser weld bead (WB). In any case, the base 122b includes a feed opening (O) and a tooth 124e formed in the top piece flexes (as indicated by the arrow) to allow insertion of a spring member. The tooth may overhang the feed opening at its end 144 to ensure one-way operation and further stabilize it when an associated spring member is in tension.

Tooth 124e may be defined in top piece 122a by laser or water jet cutting, etching or machining a kerf 148 with optional stress relief features (R) there through. The same approach may be taken for the feed opening (O) in the base piece. So-manufactured in SE Nitinol, the overall body 122 may be as little as about 0.020 inches in height with the top piece being between about 0.005 and about 0.010 inches thick and the base piece advantageously being between about 0.010 and about 0.015 inches thick.

Alternatively, the pieces may be produced in plastic (e.g., PEEK)—typically with slightly thicker dimensions to account for material strength. Plastic pieces may be made by injection molding and/or by the same techniques used for the Nitinol, without the need for injection molding cost and/or associated feature-size, draft angle, etc. requirements or limitations. The plastic body pieces 112a, 112b may be joined or bonded by welding via laser, ultrasonics or otherwise.

Irrespective of the anchor head embodiment selected, the spring member may be pulled through and locked in tension simultaneously with the anchor head(s). When the spring member(s) is/are made of SE Nitinol, stable positioning of the heads (i.e., anchoring) will typically occur before any Stress Induced Martinsite (SIM) formation occurs in the spring member(s). In any case, stable anchor position is achieved with as few as a one or two "clicks" of an anchor's ratcheting interface with the spring member—especially in cases where the anchors or optional underlying washers include pinning or other frictional interface features such as described above.

Tensioning or preloading the spring member after initial anchoring may involve drawing the spring member through the anchor head(s) by about 0.1 inches or up to about 0.25 inches or more depending on the length of the spring member and indication to be addressed. The degree or magnitude of the resulting operative tensioning can be tracked and/or calculated based on the number of beam pairs (or spring member bridges) pulled through the anchor head(s) ratcheting interface—e.g., by "counting clicks" (after removing system slack for anchoring) in reference to an algebraic formula, look-up table and/or Instructions for Use (IFU) recommendation(s). Otherwise, a standard or customized force gauge can be employed.

A given spring member is typically tensioned axially such that possible migration of its anchor features inward will not leave the spring member loose or slack. As such, it will continue to deliver "active" tension in use. This provides a key advantage for optimal healing of a fracture or osteotomy, and for stabilization and healing of a syndesmosis or joint with limited range of motion.

Figure 4A:
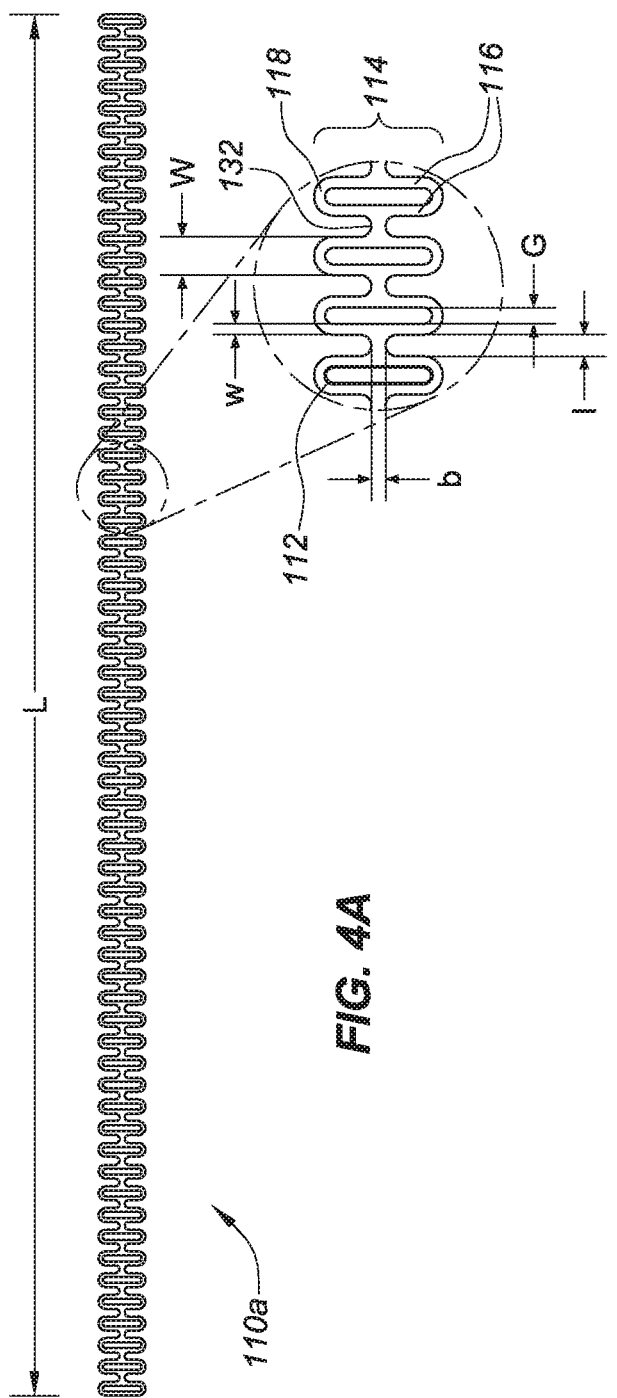
FIGS. 4A and 4B are side views (each with an inset detail view) of elongate spring member configurations or embodiments hereof.
Figure 4B:
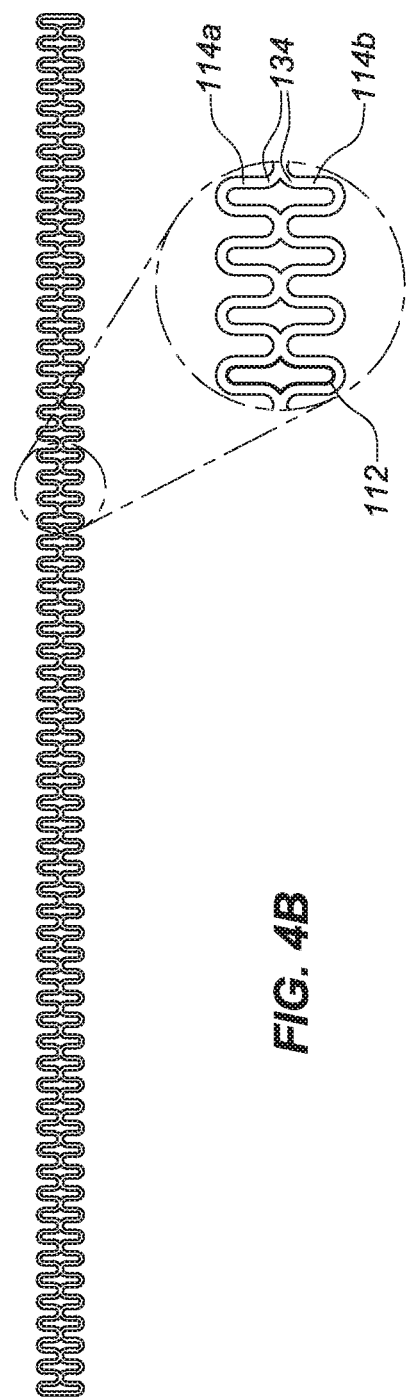

Various configurations are possible for the spring member (as are anchoring approaches as further discussed below). FIGS. 4A and 4B provide side views of alternative spring member configurations. The variation 110a shown in FIG. 4A is like that shown in FIG. 2. It includes a plurality of beams 114 where the beams each include a lateral bar component 116 to deflect for stretching the spring member axially. In the spring pattern, lateral bars 116 are provided in opposing pairs joined to each other at an outer extent connector 118 of each beam. Each such connector may be a curved continuation of each bar or beam member. Each pair of beams is connected to an axially adjacent pair by a medial connector or bridge 132.

Little to substantially no longitudinal flex or extension occurs at the bridges 132 and/or outer connectors 118 when stretching the overall spring member. Rather, they experience bending loads associated with flexure of the lateral beam elements 114. The pattern of spring member 110b in FIG. 4B is modified somewhat without change in operative principle.

Here the beams are broken into two segments 114a, 114b by formation of crown sections or segments 134 that are also involved in the bridge section 132. Such use of the crowns may improve beam segment flexibility by freeing flexure at junction (J).

The pattern in FIG. 4A may sometimes be preferred, however, in that the central flat (F) section offers a clean interface for an anchor head tooth 124. Naturally, hybrid variations (i.e., with anchor-interfacing sections resembling the cutout pattern in FIG. 4A and other sections where no such activity is expected resembling the pattern in FIG. 4B).

In the variations shown, beam width (w) is about 0.008 inches, overall width (W) is about 0.09 inches, tooth gap (G) about 0.014 inches. Overall length (L) is about 3 inches. Bridge length (l) is about 0.012 inches and bridge width (b) is about 0.012 inches (disregarding radii). Of course, these dimensions are merely exemplary and may be further refined for a selected use, method or application by those with skill in the art. However, devices configured with the noted dimensions (e.g., with an overall thickness (T) ranging from about 0.035 to about 0.040 inches) offer some notable performance features. Excellent extension and lateral flexibility is observed. As is some asymmetry in the lateral bending potential. The asymmetry can offer advantage in some methods where the elongate spring member may be oriented or "clocked" preferentially in one direction (e.g., with overall width (W) oriented from noon-to-six o'clock position) or another (e.g., with W oriented from three-to-nine o'clock position) in order to offer greater stabilization and/or mobility around a selected axis or in a selected plane.

As for use, FIG. 5A illustrates a navicular bone 200 with a fracture 202. In FIG. 5B, the bone 200 is shown mended or treated using a variation of the subject system 150. This system 150 differs from system 100 in FIG. 2 by inclusion of a distal anchor foot 160 instead of a second head 120 (although a two-headed approach could be used to treat bone 200). System 150 allows continuous compression of the fracture by minimally invasive means with minimal drilling of bone. Further structural details and details of the foot are discussed below.

With the fracture 202 reduced to an anatomic position, it is subjected by the device to a compressive force that will continue without relaxation as long as system 150 is tensioned and anchored in place. After it is so-tensioned, the proximal end of the spring member 110 may be trimmed flush as indicated by the dashed line with end nipper other cutting pliers. Alternatively, a modified version of a cable tie tool or so-called "zip-tie gun" 300 may be used to automatically or semi-automatically tighten and trim the system.

With respect to anchor foot 160, FIGS. 6A/7A and 6B/7B illustrate various optional features. Each of the versions employs a foot 160 in the form of a flat or flattened rectangular body. The foot advantageously includes a transverse groove 162 to serve as a pivot line around a distal end beam 114 of the spring member. As indicated by the dashed line in FIG. 6B, the height of the foot may also be cut down or relieved by an amount to define an inset or relief feature (R) to accommodate the spring member when the foot pivots. Such an inset or relief feature can reduce the drill size required to install the device.

As shown in FIGS. 6A and 6B, the foot may be held in communication with the final distal beam of the spring member by filament(s) or a cord strand 170 that is looped through the bodies (e.g., through a spring member aperture 112 and a channel or through holes—not shown—in the foot) and tied with a knot 172. As shown in FIG. 6B, the strand may be cut with a scalpel 302 or other surgical instrument to release the foot from the spring member for proximal retrieval of the a majority of the system after it has served its purpose.

A more complex attachment arrangement with a pass-through or looped strand 174 is illustrated in FIGS. 7A and 7B. Here, the loop is held in place until rod 180 is pulled free. The rod may include a threaded proximal interface 182 for mating with an extraction cannula 190 to permit remote access. Position of the rod may be maintained by use of an optional sheath 140 or guides (not shown). Also, rod 180 may include a distal "tail" section 184 that interfaces with a gap 112 in the spring member. This can be employed as a temporary lock that is released when pulling the rod proximally with sufficient force to plastically, elastically or superelastically as in the case where the rod comprises SE Nitinol.

Whether employing such features or not, FIGS. 8-14 further illustrate the subject embodiments (i.e., systems 100 and/or 150) in use. These figures offer a limited representation of medical methods that may be accomplished given the platform utility offered by the various embodiments described and others made possible based on this disclosure.

Figure 8:
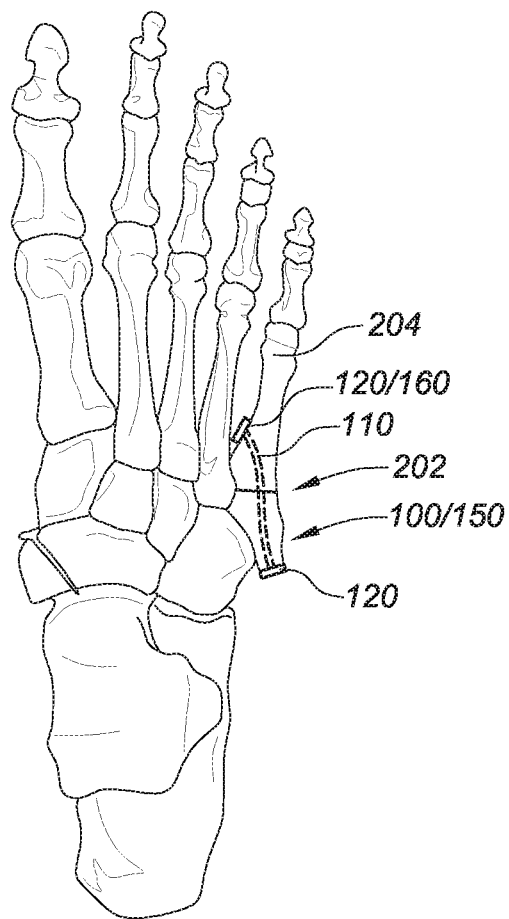

Referring to FIG. 8, it shows fixation of a fifth metatarsal 204 meta-diaphyseal fracture (commonly referred to as a "Jones" fracture). The spring member 110 is advanced through a small diameter drill hole formed approximately orthogonal to the fracture 202. If system 150 is used, an attached foot 160 is deployed distally and an anchor head 120 is attached proximally with the spring member then tensioned to supply continuous compression to the fracture. Such an approach could be applied to fractures of various orientations in the fifth metatarsal and other tarsal and metatarsal bones. The method may similarly be accomplished with a system 100 in which the distal anchoring member is a head 120 (vs. a foot 160).

Figure 9:
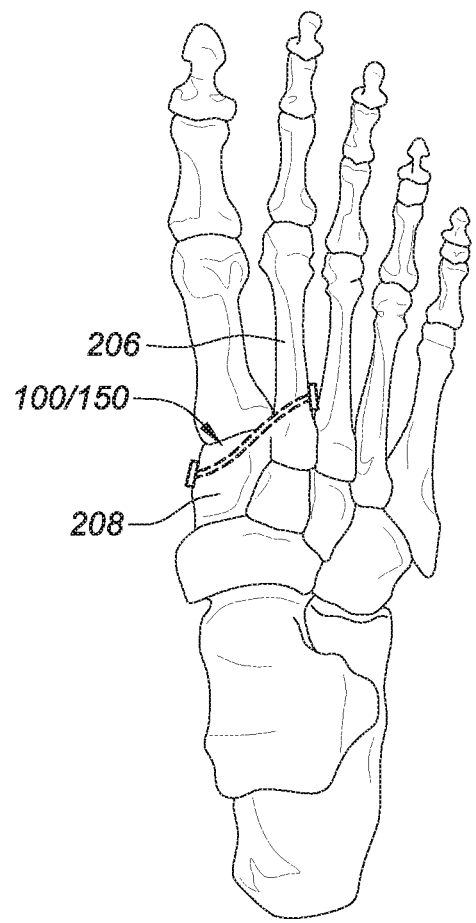

FIG. 9 illustrates stabilization of a ligamentous "Lisfranc" injury between the second metatarsal 206 and medial cuneiform 208. After ligamentous disruption, the articulation is stabilized by placement of the flexible spring member 100 or 150 (with anchor heads 120 or a head 120 and distal foot 160, respectively) though a drilled hole. Then with a/the proximal anchor 120 fit over the spring member, spring member 110 is tensioned to effect distraction against the distal foot or anchor head for compression. The system can be placed percutaneously, although the standard is open reduction of the injury.

Figure 10:
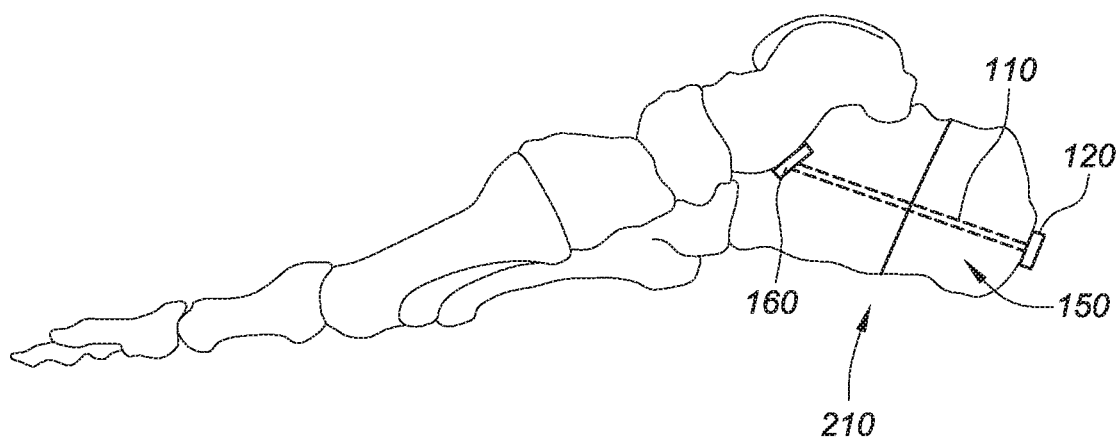

FIG. 10 illustrates a system 150 with a distal foot 160 deployed and a proximal anchor head 150 set between a spring member 110 compressing a calcaneal osteotomy 210. The system can be employed with a medializing, lateralizing, or closing wedge osteotomy. System 150 (used with or without the addition of a sheath 130 and/or washers 132—as is the case with the other procedures referenced herein) is able to provide continuous compression, stabilizing the osteotomy, with very little added bulk, and small (e.g., 4 mm or less) diameter drill hole for passing foot 160 and receiving spring member 110 and/or sheath 130.

FIGS. 11A and 11B, illustrate a system 100 or 150 stabilizing a proximal tibio-fibular joint 212 after acute or chronic ligamentous disruption of the joint. The selected system can be placed and/or tensioned (to exert appropriate compression on the joint) percutaneously.

FIG. 12 illustrates use of two systems 100 and/or 150 for a tibiofibular syndesmotic injury 214. Appropriate compression is applied and the two systems set slightly divergent for maximizing the stability of the joint while still allowing a micro-motion environment optimal for ligament healing. Such an approach provides many of the advantages of solid screws and many of the advantages of suture-button type devices, with few of the disadvantages. The systems can be inserted and tightened percutaneously. They can also be placed through a standard (or customized) fracture fixation plate in cases of an associated fracture that requires fixation.

Figure 13:
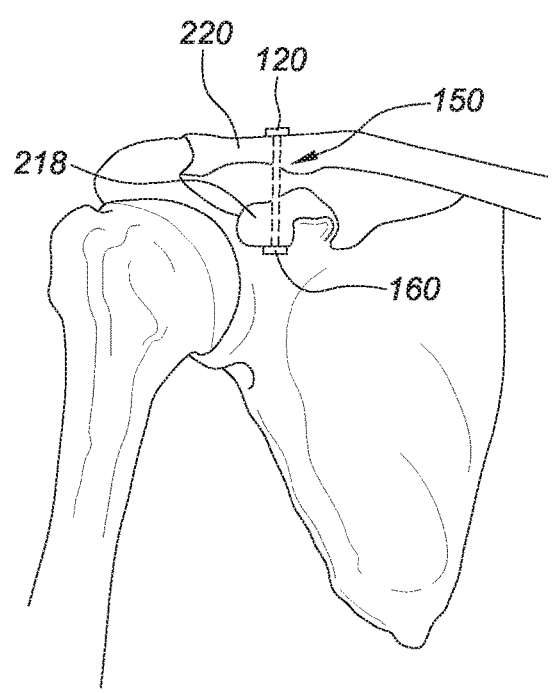

FIG. 13 illustrates use of system 150 with a distal foot 160 and proximal or near-side anchor 120 for fixation of an acromioclavicular injury 216 with ligamentous disruption. In use, foot 160 is secured by insertion through a drill hole in the coracoid process 218. Upon tensioning, proximal anchor 120 rests against the clavicle cortical bone 220.

Figure 14:
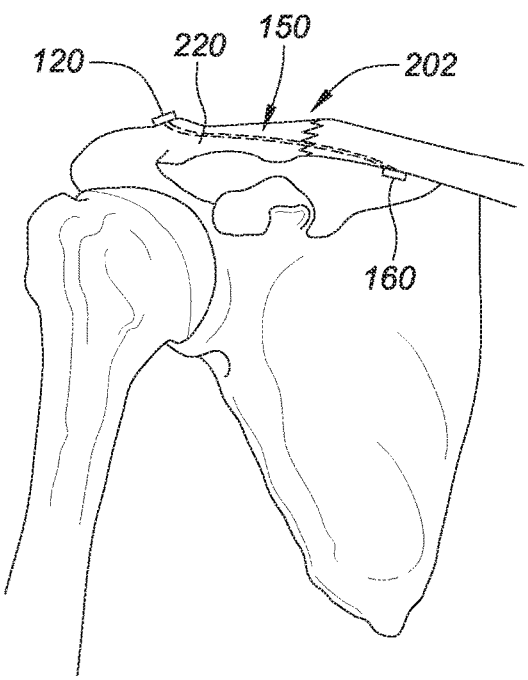

FIG. 14 illustrates fixation of a clavicle bone 220 with an oblique fracture 202 with a system 150. Here, spring member 110 and foot 160 are inserted through drill hole from the dorsal lateral cortex to plantar medial. Upon achieving appropriate compression via spring member tensioning with a proximal anchor 120, excess spring member 110 length is trimmed off (as it is in the other procedures) prior to closing the access incision (again, as in the other procedures).

Figure 15:
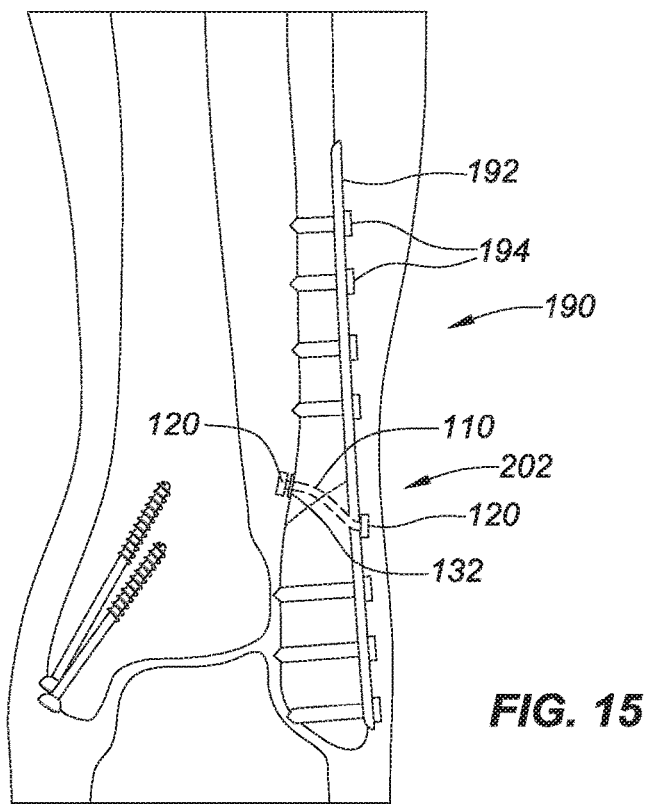
FIG. 15 is a radiographic image illustrating another embodiment system in use.

There are additional indications for the system or device embodiments hereof in settings where continuous compression is necessary or optimal and/or minimally invasive approaches are beneficial. FIG. 15 is a radiographic image providing another such example where a system embodiment 100 or 150 orthogonally spans a fracture 202 of a fibula 214 to allow continuous compression at the fracture site.

As well understood, optimal fracture healing requires reduction of the fracture (i.e., correction of the fracture edges to an anatomic alignment), bone contact, compression of the fragments together, and mechanical stability. The current standard for treatment of many long bone fractures (e.g., tibia, fibula, femur, metatarsals, metacarpals) includes treatment with a lag screw placed orthogonal to the fracture site, and a plate to stabilize the bones. The lag screw is designed to apply compression at the fracture. However, it does not apply continuous compression after the device is employed.

In FIG. 15, system 190 includes an elongate spring member 110 that passes through a fracture stabilizing plate 192 which is secured with screws 194. Such an approach allows administration of as much manual compression as needed (based on stability, bone quality, etc.), and continuous compression during fracture healing provided by spring member 110. The approach may accelerate bone healing and enhance injury recovery. In system 190, separate anchors 120, or a substitute distal foot 160 (not shown), may be employed for securing spring member 110. Alternatively, the stabilizing plates 192 may include the ratcheting tooth feature(s) 124 otherwise used in an anchor head to secure the spring member.

In this method and others, sufficient compression for fracture healing is achieved by tensioning the spring member to an operative or operating force that may be between about 2 to about 5 pounds of force (lbf)—coinciding with the typical maximum force of an "AO" lag screw otherwise used. The subject spring member(s) will provide continuous compression across a fracture site in this range or higher as selected by the physician through discrete, incremental, ratcheted, click-type tightening of the spring to aid in expeditious healing.

Variations

In addition to the embodiments disclosed already, still more variations are within the scope of this description. The subject methods, including methods of use and/or manufacture, may be carried out in any order of the events which is logically possible, as well as any recited order of events. Medical methods may include any of a hospital staff's activities associated with device provision, implant positioning, re-positioning, element (such as an anchor foot) release, retrieval and/or removal of some or all of the system components (e.g., it is specifically contemplate that the foot and/or sheath members may be left in place as part of a procedure while other components are removed).

Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein. Moreover, no limitations from the specification are intended to be read into any claims, unless those limitations are expressly included in the claims.

As used herein and in the appended claims, the singular forms "a", "an", and "the" include plural referents unless the context clearly dictates otherwise. In other words, use of the articles allow for "at least one" of the subject items in the description above as well as the claims below. The claims may exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

The subject matter described herein and in the accompanying figures is done so with sufficient detail and clarity to permit the inclusion of claims, at any time, in means-plus-function format pursuant to 35 U.S.C. section 112, part (f). However, a claim is to be interpreted as invoking this means-plus-function format only if the phrase "means for" is explicitly recited in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

The invention claimed is:

1. An orthopedic surgery system comprising:
a spring member comprising a NiTi alloy and having an elongate stretchable structure with two lateral outer extents, the spring member comprising a plurality of beams arranged in pairs, wherein a first beam and a second beam of each pair are connected to each other only at the two lateral outer extents such that the first beam opposes the second beam, and wherein each pair of beams is connected to an adjacent pair of beams by only a medial connector such that gaps are present at the two lateral outer extents between each pair of beams and the adjacent pair of beams; and
an anchoring foot rotatable around a pivot located at a distal end of the spring member from a position at least partially aligned with the spring member to a position transverse to the spring member.

2. The system of claim 1, wherein the pivot comprises a transverse groove in the anchoring foot interfacing with the distal end of the spring member.

3. The system of claim 2, wherein the anchoring foot is secured to the spring member with a cord.

4. The system of claim 3, wherein the cord is held by a removable rod.

5. The system of claim 1, further comprising an anchoring head.

6. The system of claim 5, wherein the spring member is received by the anchoring head.

7. The system of claim 6, wherein the spring member is engaged by a tooth in the anchoring head.

8. The system of claim 6, wherein the spring member is engaged by a single tooth in the anchoring head, wherein the anchoring head has only the single tooth.

9. The system of claim 8, wherein the single tooth comprises metal.

10. The system of claim 9, wherein the metal is selected from stainless steel and a NiTi alloy.

11. The system of claim 9, wherein the anchoring head includes a feed opening for the spring member and the single tooth crosses and overhangs the feed opening.

* * * * *